(12) United States Patent
Smith et al.

(10) Patent No.: US 9,968,758 B2
(45) Date of Patent: May 15, 2018

(54) DEVICES AND METHODS FOR TREATING A LUNG

(71) Applicant: Boston Scientific Scimed, Inc., Maple Grove, MN (US)

(72) Inventors: Paul Smith, Smithfield, RI (US); Robert B. Devries, Northborough, MA (US); Jason Weiner, Grafton, MA (US); Man Minh Nguyen, Harvard, MA (US); Gary J. Leanna, Holden, MA (US); Kevin John Wilcox, Brighton, MA (US); Javier Palomar-Moreno, Galway (IE); Fergal Horgan, County Mayo (IE); Martyn G. Folan, Loughrea (IE); Patricia Kelly, Galway (IE); Michael G. Hayes, Salthill (IE); Sean P. Fleury, Brighton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 416 days.

(21) Appl. No.: 14/664,070

(22) Filed: Mar. 20, 2015

(65) Prior Publication Data

US 2015/0265799 A1 Sep. 24, 2015

Related U.S. Application Data

(60) Provisional application No. 61/968,915, filed on Mar. 21, 2014.

(51) Int. Cl.
*A61M 31/00* (2006.01)
*A61M 25/00* (2006.01)
(Continued)

(52) U.S. Cl.
CPC ....... *A61M 25/007* (2013.01); *A61B 17/1219* (2013.01); *A61B 17/12031* (2013.01);
(Continued)

(58) Field of Classification Search
CPC .. A61M 2202/0488; A61M 2210/1025; A61M 2210/1035; A61M 2210/1039;
(Continued)

(56) References Cited

U.S. PATENT DOCUMENTS 4,674,480 A * 6/1987 Lemelson .......... A61K 41/0095
264/4.1
5,585,112 A * 12/1996 Unger .................... A61K 9/127
264/4.1
(Continued)

FOREIGN PATENT DOCUMENTS

| JP | H04 312454 A | 11/1992 |
|---|---|---|
| WO | WO 00/62699 | 10/2000 |
| WO | WO 01/02042 A1 | 1/2001 |

OTHER PUBLICATIONS

Nishi et al., "Basic Fibroblast Growth Factor Impregnated Hydrogel Microspheres for Embolization of Cerebral Arteriovenous Malformations", 1998, pp. M405-M410, vol. 44, No. 5, ASAIO Journal (6 pages).

*Primary Examiner* — Imani Hayman
*Assistant Examiner* — Leah Swanson
(74) *Attorney, Agent, or Firm* — Bookoff McAndrews, PLLC

(57) ABSTRACT

Methods and devices for treating a lung are disclosed. The method may include deploying a catheter into an airway of the lung, and discharging a media into the airway through the catheter. The media may be configured to increase elasticity of lung tissue in the vicinity of the airway or occlude the airway.

15 Claims, 7 Drawing Sheets

(51) Int. Cl.
  *A61K 31/56* (2006.01)
  *A61B 17/12* (2006.01)
  *A61B 17/00* (2006.01)
(52) U.S. Cl.
  CPC .. *A61B 17/12104* (2013.01); *A61B 17/12136* (2013.01); *A61B 17/12186* (2013.01); *A61K 31/56* (2013.01); *A61B 2017/003* (2013.01); *A61B 2017/00893* (2013.01); *A61B 2017/1205* (2013.01)
(58) Field of Classification Search
  CPC ..... A61M 2210/0618; A61B 17/12104; A61K 31/56
  USPC ....................................................... 604/514
  See application file for complete search history.

(56) References Cited

U.S. PATENT DOCUMENTS

| | | | |
|---|---|---|---|
| 6,126,919 A * | 10/2000 | Stefely | A61K 9/0075 424/426 |
| 6,493,589 B1 | 12/2002 | Medhkour et al. | |
| 6,855,153 B2 | 2/2005 | Saadat | |
| 7,556,624 B2 * | 7/2009 | Laufer | A61B 18/00 604/514 |
| 7,913,698 B2 | 3/2011 | Barry et al. | |
| 2002/0133148 A1 * | 9/2002 | Daniel | A61B 18/1477 606/34 |
| 2003/0070676 A1 | 4/2003 | Cooper et al. | |
| 2004/0091543 A1 | 5/2004 | Bell et al. | |
| 2004/0098023 A1 | 5/2004 | Lee et al. | |
| 2005/0196449 A1 | 9/2005 | Dicarlo et al. | |
| 2006/0004400 A1 | 1/2006 | McGurk et al. | |
| 2006/0047291 A1 | 3/2006 | Barry | |
| 2006/0235467 A1 | 10/2006 | DeVore | |
| 2008/0097139 A1 * | 4/2008 | Clerc | A61B 18/0218 600/7 |
| 2011/0071495 A1 | 3/2011 | Tekulve | |
| 2011/0208228 A1 | 8/2011 | Gonzales et al. | |
| 2011/0301587 A1 * | 12/2011 | Deem | A61B 18/1815 606/33 |
| 2012/0041412 A1 | 2/2012 | Roth et al. | |
| 2012/0053513 A1 | 3/2012 | Tada et al. | |
| 2012/0053566 A1 | 3/2012 | Tada et al. | |

* cited by examiner

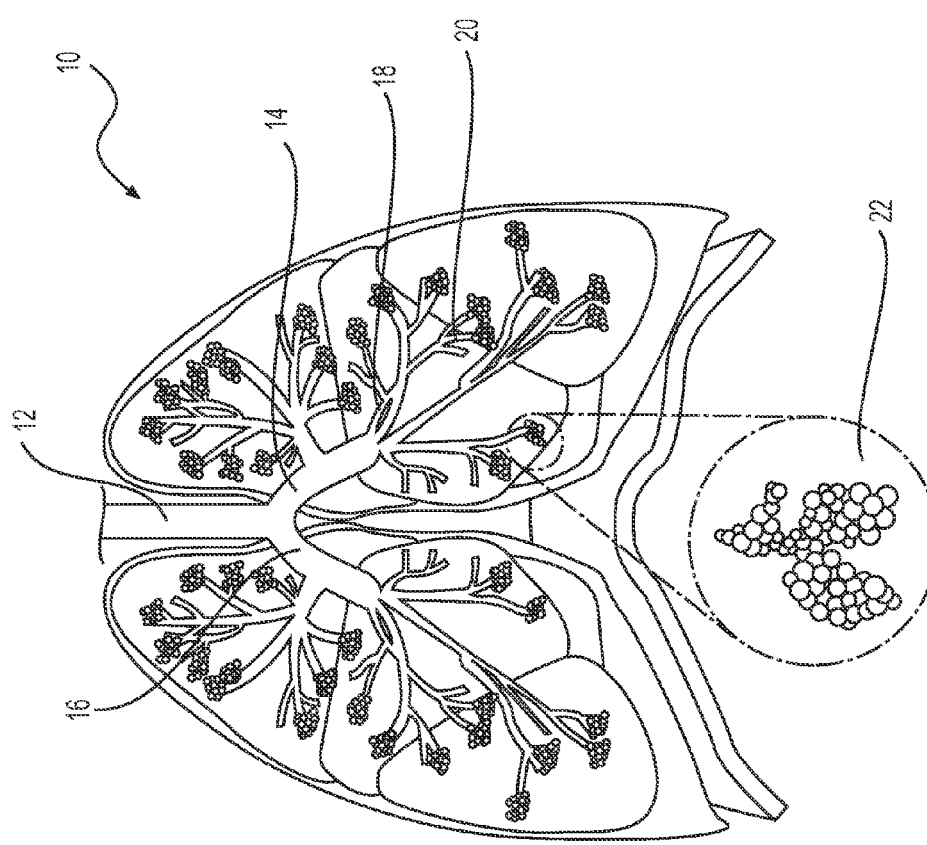

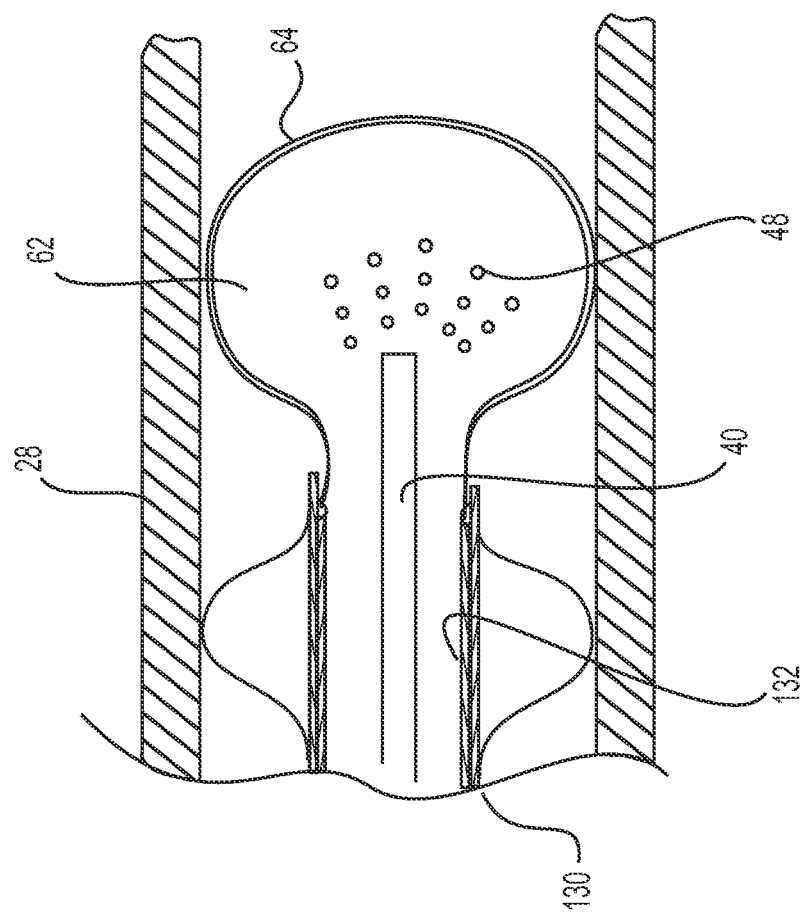

DEVICES AND METHODS FOR TREATING A LUNG

CROSS-REFERENCE TO RELATED APPLICATION

This patent application claims benefit of priority under 35 U.S.C. § 119 to U.S. Provisional Patent Application No. 61/968,915, filed Mar. 21, 2014, the entirety of which is incorporated herein by reference.

TECHNICAL FIELD

The disclosed embodiments relate to devices and methods for treating a lung and, in an embodiment, chronic obstructive pulmonary disease (COPD). More particularly, the present disclosure relates to devices and methods of treating airways of lungs.

BACKGROUND

Chronic obstructive pulmonary disease (COPD) is a serious progressive lung disease which makes it harder to breath. It currently affects over fifteen million people in the United States alone and is currently a leading cause of death in the country. The overwhelming primary cause of COPD is inhalation of cigarette smoke, responsible for over 90% of COPD cases. The economic and social burden of the disease is both substantial and increasing.

FIG. 1 depicts a healthy set of lungs 10 in an individual. A wind pipe or trachea 12 connects the nose (not shown) and mouth (not shown) to the lungs 10. As air flows in through the nose and mouth of an individual, the trachea 12 transports the air to the lungs 10 for respiratory functions. The trachea 12 divides into the left 14 and right 16 bronchus stems, which further divide into a plurality of bronchi 18, bronchioles 20, and eventually, terminate in a plurality of alveoli 22. The alveoli 22 are small air sacs which enable gas exchange with the individual's blood stream. That is, they permit oxygen diffusion into the blood stream, and receive and expel $CO_2$ during exhalation.

COPD includes emphysema. As shown in FIG. 2A, emphysema may be characterized by the destruction of lung parenchyma 24, the functioning parts of the lungs 10. The parenchyma 24 includes the alveoli 22 walls, bronchioles 20, and the bronchi 18. Destruction of these tissues results in progressively increasing shortness of breath called dyspnea. As it worsens, emphysema turns the healthy alveoli 22, clustered like bunches of grapes, into large, irregular pockets with gaping holes in their inner walls, as shown in FIG. 2B. This reduces the surface area of the lungs and, in turn, the amount of oxygen that reaches an individual's blood stream.

Destruction of the lung parenchyma may also lead to loss of elastic recoil and tethering (i.e., ability to hold open walls of airways, including the bronchioles 20, leading to the alveoli 22 throughout much of inhalation and expiration), which maintains airway patency. Unlike larger lung airways, the bronchioles 20 are not supported by cartilage and thus have little intrinsic support. As a result, the bronchioles 20 are susceptible to collapse or reduction in diameter when destruction of tethering occurs, particularly during exhalation. The collapse of airways may prevent air in the alveoli 22 from escaping during exhalation. A significantly reduced diameter airway 26 connecting to an alveoli 22 is depicted in FIG. 2B. This trapped gas in the alveoli 22 may lead to hypercapnia (high levels of $CO_2$ in the blood stream) and acidosis (lowering of pH levels), which are correlated to mortality in COPD patients.

One existing approach to treat emphysema is performing lung volume reduction surgery, which removes or kills a portion of a diseased lung to allow greater expansion of remaining lung tissue. However, this approach poses a substantial risk due to its invasive nature. It may, therefore, be beneficial to provide a less-invasive technique for treating emphysema, or other lung conditions including asthma.

SUMMARY

The disclosed embodiments relate to devices and methods for manipulating lung airways in a patient for treating, for example, chronic obstruction pulmonary diseases. In one exemplary embodiment, a method of treating a lung is disclosed. The method may include deploying a catheter into an airway of the lung, and discharging a media into the airway through the catheter. The media may be configured to increase elasticity of lung tissue in the vicinity of the airway.

The disclosed method may include one or more of the following features. Discharging the media may include chemically washing the airway using the media; the injectable media may be one of (i) a polymer, (ii) an oil, (iii) a gel, (iv) a surfactant; discharging the media may include injecting the media into the airway using a needle fluidly coupled to a distal end of the catheter; and discharging the media may include injecting the media into a tissue of the airway.

In another exemplary embodiment, a method of treating a lung is disclosed. The method may include deploying a catheter into an airway of the lung, and discharging a media into the airway through the catheter. The media may be configured to expand in the airway and occlude the airway after being discharged from the catheter.

The disclosed method may include one or more of the following features. The method may include a plurality of the media, wherein the plurality of media may interlock together in the airway after the discharging; and wherein the media may include a drug, and the method may include releasing the drug into the airway from the media after the discharging.

In another exemplary embodiment, a device for treating an airway of a lung is disclosed. The device may include an injectable media configured for deployment into an airway of the lung. The media may be configured to expand in the airway and occlude the airway. The device may also include a catheter configured for insertion into or proximate the airway. The catheter may be configured to discharge the media into the airway.

The disclosed device may include one or more of the following features. A surface of the media may include features configured to interlock with each other; the media may include one of fibers, particles, or beads, and an average particle size of the media may be less than 300 microns; and the media may be drug-eluting.

In another exemplary embodiment, a method of treating a lung is disclosed. The method may include deploying a catheter into an airway of the lung, and depositing a pattern of a media into the airway through the catheter. The pattern may be helicoidal. The media may include a drug suspension in a biodegradable polymer.

The disclosed method may include one or more of the following features. Depositing a helicoidal pattern may include discharging the media from the catheter while the catheter is rotated and translated; the biodegradable polymer may include a low glass transition temperature; depositing a pattern may include discharging the media into the airway in a fluid form, and solidifying the media in the airway; discharging the media may include heating the media above a glass transition temperature of the polymer, and solidifying the media may include cooling the media below the glass transition temperature; and the drug may include a corticosteroid or a glucosteroid.

In another exemplary embodiment, a device for treating a lung is disclosed. The device may include an injectable media. The injectable media may be a drug suspension in a biodegradable polymer. The device may also include a catheter configured to deposit a pattern of the injectable media in an airway of the lung.

The disclosed device may include one or more of the following features. The catheter may include a substantially L-shaped tip; the catheter may include a heating element or an energy transfer element (for example, a heater) configured to maintain the injectable media in a liquid state; the device may also include a rotating mechanism configured to rotate the catheter as the injectable media is discharged into the airway.

The above summary of exemplary embodiments is not intended to describe each disclosed embodiment or every implementation of the present disclosure. The figures and the description, which follow, more particularly exemplify these embodiments.

BRIEF DESCRIPTION OF THE DRAWINGS

The drawings illustrate the design and utility of exemplary embodiments of the present disclosure, in which similar elements are referred to by common reference numerals. In order to better appreciate how the above-disclosed and other advantages and objects of the present disclosure are obtained, a more detailed description of the present embodiments will be rendered by reference to the accompanying drawings. Understanding that these drawings depict only exemplary embodiments of the disclosure and are not therefore to be considered limiting in scope, the disclosure will be described and explained with additional specificity and detail through the use of the accompanying drawings in which:

FIG. 1 illustrates the anatomy of healthy lungs of an individual;

FIG. 8 illustrates another exemplary embodiment of the distal end of a device for deploying an exemplary media in an airway of the lung of FIG. 2A.

DETAILED DESCRIPTION OF EXEMPLARY EMBODIMENTS

The present disclosure is drawn to devices and methods for the treatment of diseased tissue. Such diseased tissue may suffer from COPD and/or other lung conditions, such as asthma. Exemplary embodiments are drawn to devices and methods for the treatment of diseased tissue in the lungs. In some embodiments, the treatment may include repairing or rejuvenating the diseased tissue to improve overall lung function. In other embodiments, the treatment may include occluding (or blocking) one or more airways of the lungs to prevent inhaled air from reaching diseased tissue. As inhaled air is no longer directed to the diseased tissue, the remaining healthy tissues receive more air, and lung function improves. While the principles of the present disclosure are described with reference to treatments for the lungs of a patient, it should be understood that the disclosure is not limited thereto. Rather, the devices and methods may find applicability for the treatment of any luminal tissue structure.

Figure 2B:
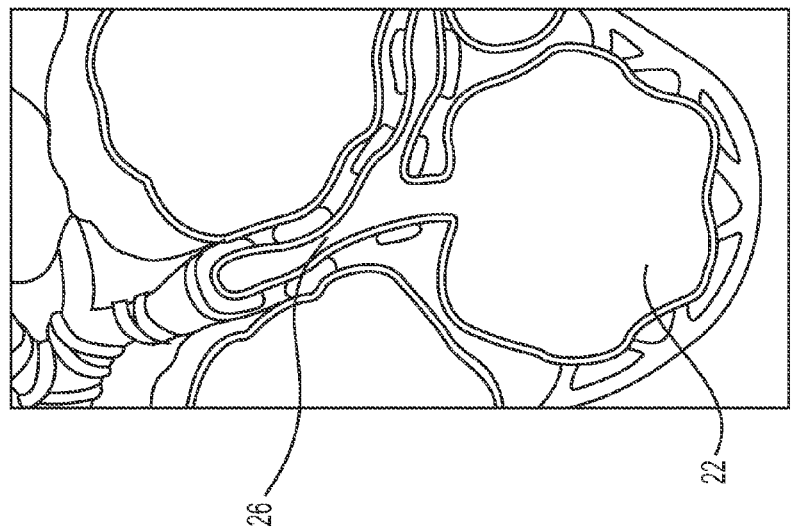
FIG. 2B is a diagrammatic illustration of an airway connected to an alveoli in the lung of FIG. 2A.
Figure 2A:
FIG. 2A illustrates a lung suffering from emphysema.
Figure 3:
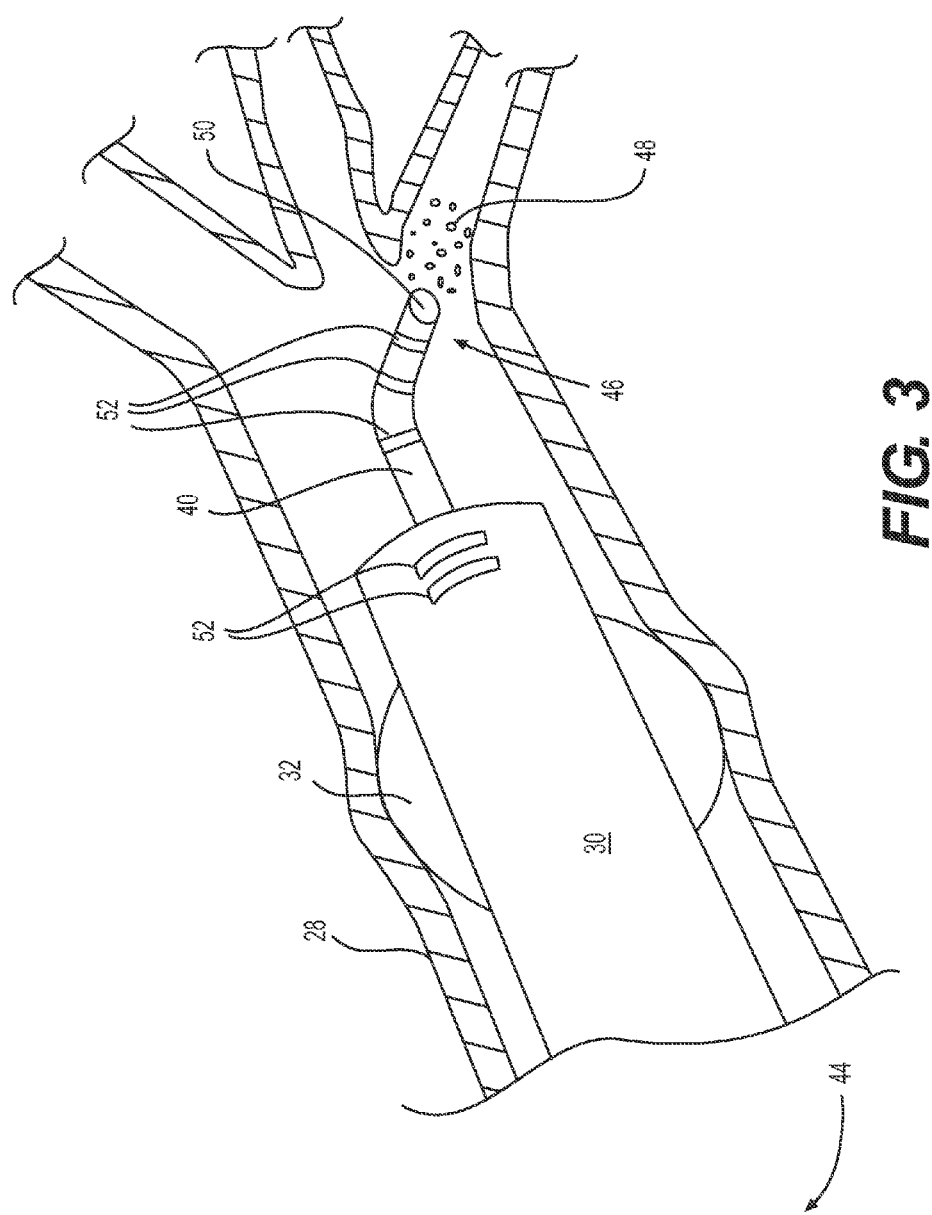
FIG. 3 illustrates an exemplary embodiment of a device for deploying an exemplary media in an airway of the lung of FIG. 2A.

FIG. 3 depicts a lung airway 28 including an exemplary embodiment of a device therein. In this disclosure, the term "airway" is used to refer to any of bronchi 18, bronchioles 20, and alveoli 22. Airway 28 may include diseased tissue, or may be positioned adjacent to diseased tissue. A user (such as, a physician, etc.) may introduce an introducer sheath 30 through the patient's airway 28 until a distal end of the sheath 30 reaches a target tissue area within airway 28. Sheath 30 may be introduced into the airway 28 via any appropriate method. In an exemplary embodiment, sheath 30 is inserted into the patient through the mouth (or another opening) and advanced into the airway 28. The sheath 30 may be sized to access the airway (i.e. bronchi 18, bronchioles 20, or alveoli 22) that is desired to be treated. In some embodiments, one or more light sources (fiber optic cables, light-emitting diodes, etc.) and/or image sensors may be provided on, or associated with, the sheath 30 to assist the user in navigating the sheath 30 through tortuous airways 28 in the patient's body. In some embodiments, the sheath 30 may also include one or more radiopaque markers 52 to assist the user in determining the proper location of the sheath 30 within the airway 28. As is known in the art, radiopaque markers 52 are indicators that are placed at strategic locations on a catheter for visibility under x-ray fluoroscopy or radiography. The sheath 30 may be introduced into the airway 28 directly, or may be introduced through a lumen of another device, such as, for example, a bronchoscope, endoscope, etc. While sheath 30 is referred to and described herein, it is to be understood that any luminal delivery device may be used without departing from the scope of the disclosure.

In some embodiments, the sheath 30 may include a retention member such as, for example, balloon 32, configured to transition between an uninflated (or deflated) configuration (not shown), and an inflated configuration (as shown in FIG. 3). Balloon 32 may expand within the airway 28 to position the sheath 30 within the airway 28. Accordingly, the balloon 32 may be configured to receive a source of inflation fluid through an inflation channel (not shown) in sheath 30. In some embodiments, the sheath 30 may include means to remove air from the balloon 32 distal to the balloon 32. The sheath 30 may be introduced into the airway 28 while the balloon 32 is in the uninflated configuration (not shown). Upon reaching the desired treatment area, the balloon 32 may be inflated. Alternatively, any suitable expandable member may be employed such as, for example, mechanical expansion cages, expandable foam members, hook and/or finger members, and expanding members activated by body heat or chemistry. In some embodiments, the balloon 32 (or any alternative expanding member) may include agents or drugs (such as, for example, antimicrobial agents, analgesics, and anesthetics, etc.) to treat the airway tissue it contacts.

An exemplary medical tool may be introduced into the airway 28 through the sheath 30. In some embodiments, the medical tool may include a steerable catheter 40. The catheter 40 may extend from a proximal end 44, positioned external to the airway 28, to a distal end 46 that extends out of the sheath 30. The distal end 46 of the catheter 40 may be positioned proximate the desired treatment site (for example, diseased tissue) in the airway 28. The catheter 40 may also include one or more radiopaque markers 52 to assist in suitably positioning the catheter 40 in the airway 28. The catheter 40 may be configured to direct an injectable media 48 into the airway 28 through its distal end 46. The proximal end 44 of the catheter 40 may include one or more steering dials (or other mechanisms) configured to articulate (or turn) the distal end 46 of the catheter 40 in different directions. This steering capability enables the catheter 40 to release the media 48 in any desired direction (for example, towards a bronchiole 20 leading to diseased alveoli 22 (see FIG. 1)).

The distal end 46 of the catheter 40 may include one or more orifice(s) 50 adapted to discharge the media 48 into the airway 28. In general, the orifice(s) 50 may be of any size and shape, and arranged in any pattern. In some embodiments, as illustrated in FIG. 3, the distal-most tip of the catheter 40 may be open to form a single orifice 50. Although the catheter 40 is described as being introduced into the airway 28 through the sheath 30, this is not a requirement. In some embodiments, the sheath 30 may be eliminated and the catheter 40 may be introduced into the airway 28 directly, or via a luminal delivery device, such as a bronchoscope. In some embodiments, the catheter 40 may also include a retention member (such as, balloon 32 of sheath 30) to maintain the position of catheter 40 within the airway 28.

Figure 4A:
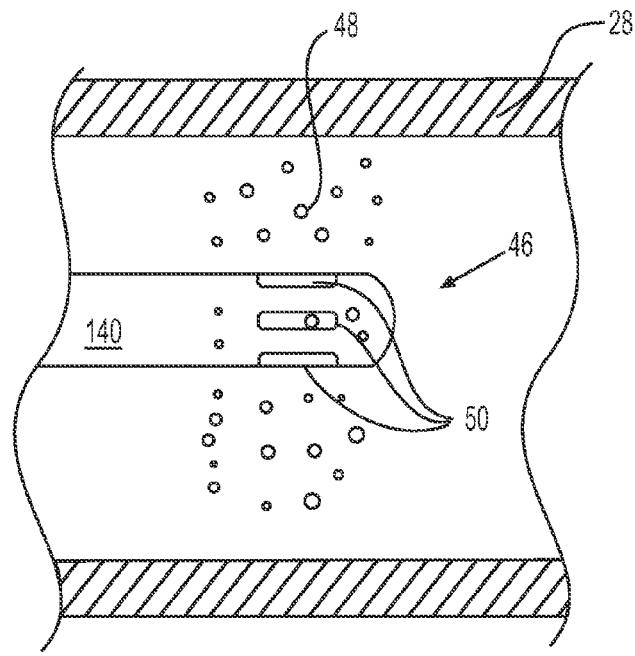
FIGS. 4A and 4B illustrate exemplary embodiments of the distal ends of a device configured to deploy media in an airway of the lung of FIG. 2A.
Figure 4B:
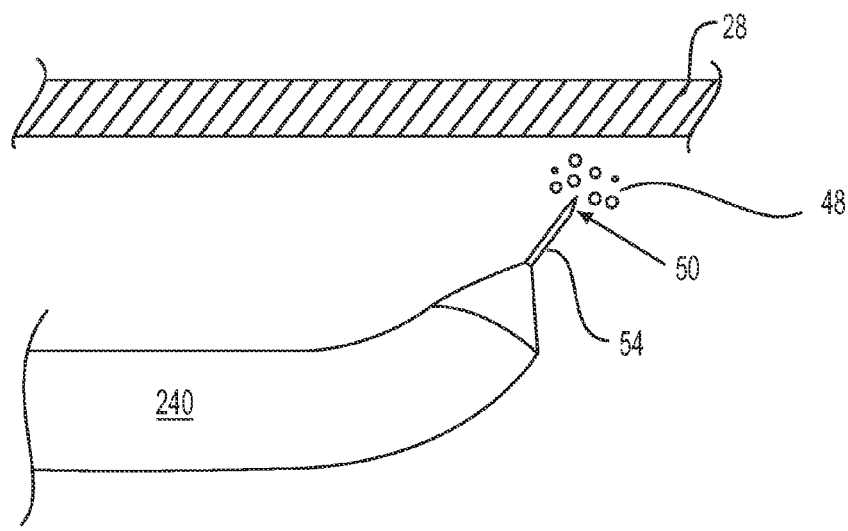

FIGS. 4A-4B illustrate other exemplary embodiments of a catheter that may be introduced into the airway 28 to discharge media 48. As illustrated in FIG. 4A, in some embodiments, a catheter 140 may include a plurality of orifices 50 arranged around its distal end 46. These orifices 50 may enable the injectable media 48 to be substantially evenly disbursed around the distal end 46 of the catheter 140. Although illustrated as being substantially rectangular, these orifices 50 may have any shape. In some embodiments, as illustrated in FIG. 4B, the distal end 46 of a catheter 240 may include a needle 54. The needle 54 may include one or more orfice(s) 50 at, or around, its tip, and may be configured to inject the media 48 into, or on, a desired region of the damaged tissue in the airway 28. In some embodiments, the needle 54 may be configured to penetrate tissue surrounding the airway 28, and discharge the injectable media 48 into the tissue and/or the muscle surrounding the tissue.

Figure 5:
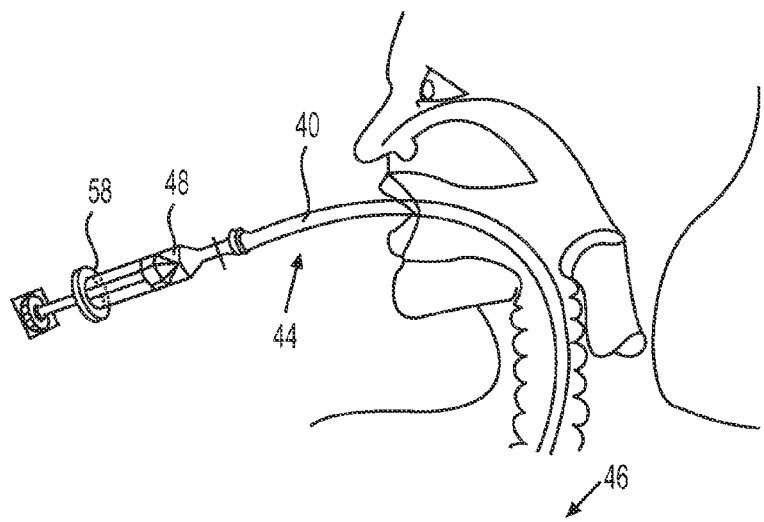
FIG. 5 illustrates the proximal end of an exemplary embodiment of a device for deploying media in an airway of the lung of FIG. 2A.

The injectable media 48 may be delivered to the distal end 46 of the catheter (40, 140, 240) from its proximal end 44. FIG. 5 illustrates one embodiment of a catheter 40 with an injector 58 containing the media 48. In some embodiments, the injector 58 may include an energy transfer element (for example, a heater) to maintain the media 48 in a heated state. Depressing a plunger of the injector 58 directs the media 48 towards the distal end 46 of the catheter 40. In use, the distal end 46 of the catheter 40 may be inserted into a patient and advanced to a desired airway 28 site. Radiopaque markers 52 (see FIG. 3) on the catheter 40 may assist in the positioning of the catheter 40 at the desired site. When the catheter 40 is suitably positioned, the user may depress the plunger of the injector 58 to discharge a desired quantity of the media 48 through the orifice(s) 50 at the distal end 46 of the catheter 40. The catheter 40 may now be moved to another location to discharge the media 48 at the new location. After all the desired locations have been treated, the catheter 40 may be withdrawn from the body.

Media 48 may be discharged into the airway 28 continuously or in batches. That is, in some embodiments, the catheter 40 may deliver a first batch of media 48 at a first time and a second batch at a second time after the first time. Each batch may include any suitable amount (number, volume, etc.) of media 48. In some embodiments, a pressurized fluid may assist in pushing the media 48 out of the catheter 40. In such embodiments, the media 48 may be released into the airway 28 along with the pressurized fluid. In such embodiments, the catheter 40 may be coupled to a pressurized fluid source (not shown).

In addition to, or in place of injector 58, in some embodiments, the proximal end 44 of the catheter 40 may be fluidly coupled to a pump that is programmed to discharge a desired quantity of the media 48 through the catheter 40. For instance, the user may activate the pump to discharge a desired quantity of the media at the desired site. Although FIG. 5 illustrates the catheter 40 as being directly inserted into the patient, as explained previously, the catheter 40 may also be introduced into the patient through a sheath 30 or another luminal delivery device. Further, although FIG. 5 illustrates the catheter 40 inserted into the mouth of a patient, this is not a requirement. In general, the catheter 40 may be inserted into the patient through any cavity that suits the medical procedure the device is applied to.

Figure 6:
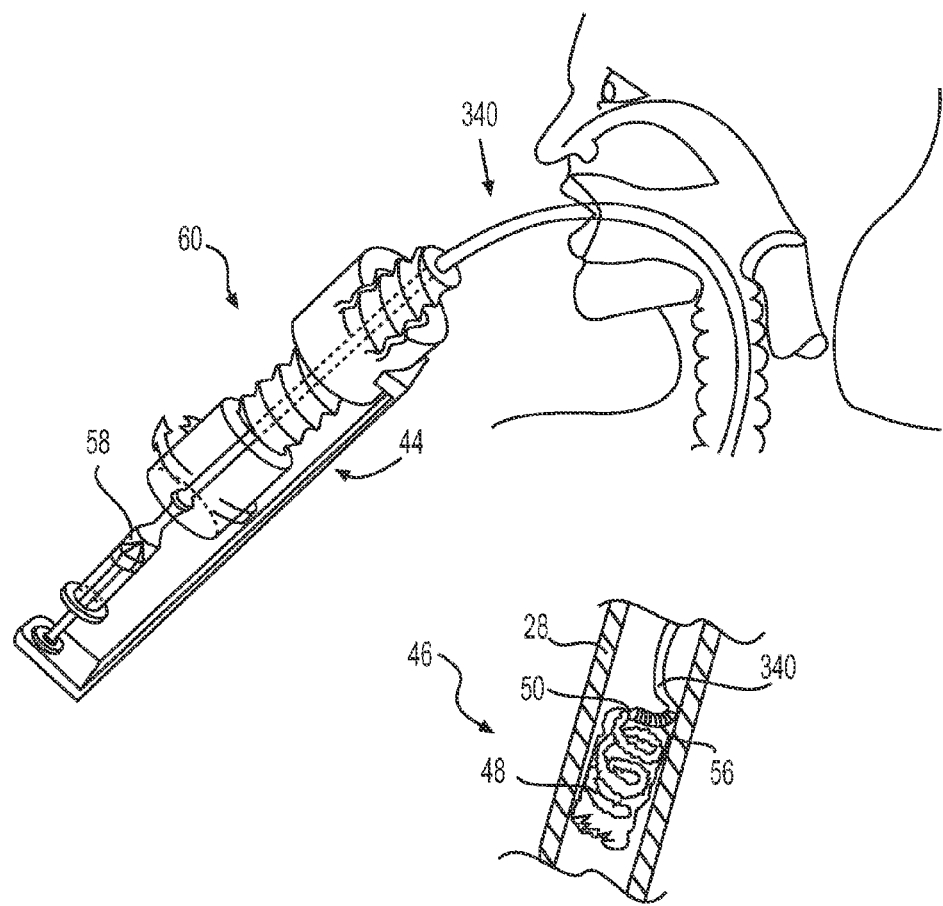
FIG. 6 illustrates another exemplary embodiment of a device for deploying an exemplary media in an airway of the lung of FIG. 2A.

FIG. 6 illustrates another exemplary embodiment of a catheter 340 that may be used to deliver a desired pattern of an injectable media 48 on an airway wall (tissue surrounding the airway 28). The distal end 46 of the catheter 340 may include a flexible substantially L-shaped tip 56 with one or more orifice(s) 50 positioned thereon. The tip 56 may be configured to press against, or be positioned proximate to (i.e. appose), the airway wall at a desired site. In some embodiments, a tip 56 having a substantially L-shape may be attached to the distal end 46 of catheter 340, while in other embodiments, the distal end 46 of catheter 340 may be bent to form a substantially L-shape after the catheter 340 is suitably positioned in an airway 28. In use, catheter 340 may be inserted into a patient and advanced to the desired site in the airway 28. The substantially L-shaped tip 56 may then be positioned apposed to the airway wall and the media 48 discharged through the orifice 50. In embodiments where the shape of the tip 56 is formed by flexing the distal end 46 of the catheter 340, the distal end 46 of the catheter 340 may be bent to position the orifice 50 proximate the airway wall before the media 48 is discharged.

To form a desired pattern of the media on the airway wall at the desired site, the catheter 340 (and tip 56) may be moved as the media 48 is released. For instance, to deposit the media 48 along a straight line, the catheter 340 may be advanced into, or retracted from, the airway 28 as the media 48 is released. To deposit the media 48 as an annular ring on the airway wall, the catheter 340 may be rotated as the media 48 is discharged. In some embodiments, the catheter 340 may be rotated and translated (advanced and/or retracted) as the media 48 is being discharged. In such embodiments, the discharged media 48 may form a helicoidal coating or pattern on the airway wall. In some embodiments, the catheter 340 may be moved (rotation, translation, etc.) manually by the user as the media 48 is released. In other embodiments, a mechanism may assist in moving the catheter 340 as the media 48 is discharged. Any suitable mechanism may be used to move the catheter 340. In some embodiments, as illustrated in FIG. 6, the proximal end 44 of the catheter 340 may be coupled to a rotating mechanism 60 that rotates and translates (advances or retracts) the catheter 340 as the injector 58 is operated. In the exemplary embodiment of the rotating mechanism 60 illustrated in FIG. 6, depressing the plunger of the injector 58 may rotate threaded shafts, and blocks that turn on these shafts, to translate and rotate the tip 56 as the media 48 is released.

Any suitable injectable media 48 may be delivered to the airway 28 using the catheter (40, 140, 240, 340). In some embodiments, media 48 may be a drug suspension mixed with a biodegradable polymer having a low glass transition temperature ($T_g$), such as for example about 45° C. In an exemplary embodiment, media 48 (in the form of a drug suspension in a biodegradable polymer) may be heated and maintained in a semi-fluid (or gel) state in the injector 58 of FIG. 6. The catheter 40 may then inserted into the patient and advanced to the desired treatment site. At the treatment site, the tip 56 may be positioned proximate the airway wall, and the media 48 released as the catheter is rotated and retracted (or advanced). The combined rotation and translation of the tip 56 may deposit the media 48 in a helicoidal pattern on the airway wall. As the media 48 cools below its $T_g$ (for example, below about 45° C.) it solidifies on the airway wall. The catheter 40 may then be moved to deposit a helicoidal pattern of the media 48 on other desired treatment sites.

Any drug, without limitation, may be mixed with the biodegradable polymer to form the media 48. In some embodiments, the drug may include long acting corticosteroids, glucocorticoids, long acting beta2-adrenergic (LABA) receptor argonists, and combinations thereof. Exemplary drugs that may be present in some embodiments of media 48 may include hydrocortisones (such as, for example, hydrocortisone, hydrocortisone acetate, cortisone acetate, tixocortol pivalate, prednisolone, methylprednisolone, and prednisone), acetonides (such as, for example, triamcinolone acetonide, triamcinolone alcohol, mometasone, amcinonide, budesonide, desonide, flucocinonide, fluocinolone acetonide, and halcinonide), betamethasones (such as, for example, betamethasone, betamethasone sodium phosphate, dexamethasone, dexamethasone sodium phosphate, and fluocortolone), halogenated drugs (such as, for example, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate, and flupredenidene acetate), labile producing esters (such as, for example, hydrocortisone-17-butyrate, 17-aceponate, 17-buteprate, and prednicarbate), steroids (such as, for example, flunisolide, fluticasone propionate, triamcinolone acetonide, beclomethasone dipropionate, budesonide), and other drugs (such as, for example ciclesonide, salmeterol, formoterol, bambuterol, clenbuterol, etc.).

Depositing a helicoidal pattern of media 48 on airway walls may have advantages. The tissue of the airway walls is composed of mucus-producing goblet cells and a ciliated epithelium (cells with hair like protrusions or cilia protruding into the airway 28). The cilia continually flex (or beat) and push mucus up and out of the airway 28 into the throat. This upward movement of mucus on the airway walls, called the mucociliary escalator, is a major barrier against infection. Microorganisms that enter the respiratory tract are caught in the sticky mucus and moved up by the mucociliary escalator. When the solidified media 48 in the airway wall contacts the mucus, the solidified polymer undergoes hydrolysis and releases the drugs mixed in the polymer. Depositing a helicoidal pattern of the media 48 on the airway wall may provide the required treatment for the wall tissue without blocking the mucociliary escalator.

In some embodiments, the injectable media 48 may be a pulmonary surfactant. Pulmonary surfactant is a compound that is naturally produced in the lungs, and is critical for proper respiratory function. Surfactants are a complex mixture of phospholipids and proteins. Surfactant reduces surface tension in the lung (which is necessary to prevent the collapse of the alveoli and other airways 28) and reduces the effort needed to expand the lungs during inhalation. The absence of sufficient surfactant leads to collapse of airways 28 and compromised pulmonary function. Exogenous replacement surfactants possess the properties needed to lower the surface tension in the lungs. In some embodiments of the current disclosure, a surfactant may be injected into, or on, airway 28 tissue to rejuvenate diseased tissue in the airway 28. The injected surfactant may help the airway 28 maintain its shape and reduce surface tension, and improve (or restore) its elasticity. Improving the elasticity of the airway may enable the airway to elastically recoil during exhalation.

In some embodiments, the injectable media 48 may include air or another fluid. In such embodiments, air or another fluid may be injected on an airway 28 (such as the alveoli 22) to chemically wash the airway 28. This chemical washing may smooth muscle tone of the tissue in the airway, and restore at least some elasticity of the tissue. Improving the elasticity of the diseased tissue may restore some function to the airway 28. It is also contemplated that, in some embodiments, a drug or a chemical may be injected into the airway 28 to flush and thereby unclog an airway 28. Any chemical suitable for unclogging the airway 28 may be injected into the airway 28 for this purpose. Although the air and the chemicals may be discharged into the airway 28 by using any of the devices discussed with reference to FIGS. 3-6, in some embodiments, a catheter 40 with a distal needle 54 (see FIG. 4B) may be used for this purpose.

In some embodiments, the injectable media 48 may be a polymer, an oil, or a gel. In such embodiments, the injectable media 48 may be discharged proximate diseased tissue in the airway 28, or injected (for example, by using needle 54 of FIG. 4B) into the diseased tissue. Exemplary polymers may include synthetic viscoelastic urethane polymers such as, for example, Sorbothane®, and exemplary gels may include hydrocolloids such as, for example, Alginate. The injected material may improve the elasticity of the tissue. In some embodiments, air may be discharged into the airway 28 (such as alveoli 22) to expand the airway 28 prior to discharge of the polymeric media 48. The air and the media 48 may be delivered to the airway 28 using the same catheter 40 or by different catheters. For instance, in embodiments where catheter 40 is introduced into the airway 28 through a luminal delivery device, the air may be directed into the airway 28 through a lumen of the device and the media 48 may be discharged through the catheter 40. The air may inflate a collapsed (or decreased diameter) airway 28 and allow the polymer to coat the walls of the inflated airway 28.

As the polymer cures, its elasticity increases. This increased elasticity may rejuvenate, and improve at least to some extent, elastic recoil of the airway 28 during inhalation and exhalation.

In some embodiments, media 48 in the form of a polymer, oil, or gel may also be used to necrose diseased tissue in an airway 28. For instance, an increased amount of the media 48 may be delivered to an airway 28 (such as a bronchi 18 or bronchioles 20) to occlude the airway 28 and cause diseased airway tissue (for example, in an associated alveoli 22) to necrose. By removing poorly functioning tissue, the remaining lung tissue may work more efficiently and improve overall pulmonary function.

Figure 7A:
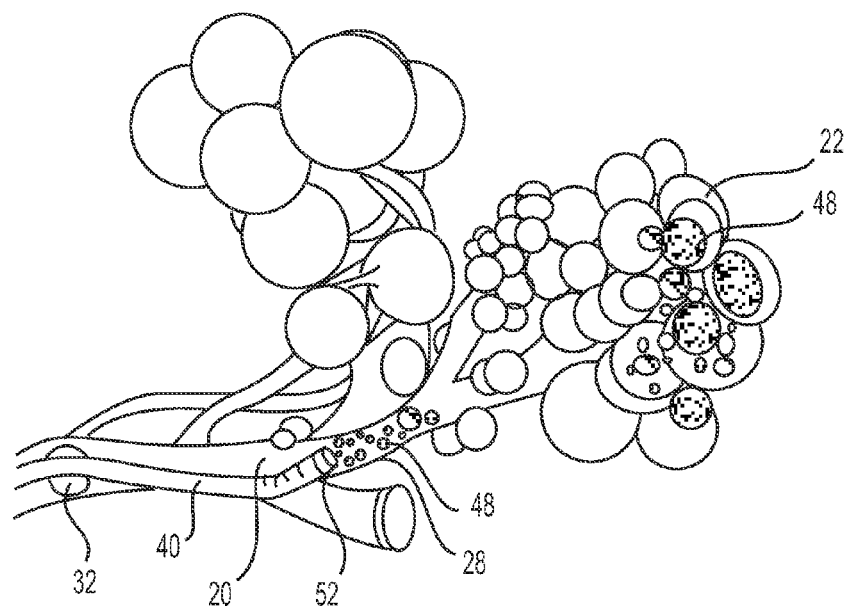
FIG. 7A illustrates another exemplary embodiment of a device for deploying an exemplary media in an airway of the lung of FIG. 2A.

In some embodiments, as illustrated in FIG. 7A, the media 48 may include a filler or occlusive material. The filler may include any type of fibers, particles, and/or beads having regular or irregular nesting shapes. In general, the fillers may have any suitable size and shape. In some embodiments, the size of the fillers may be less than about 300 microns. In some embodiments, the dimensions of the filler may be selected such that upon deployment in the airway 28, the media 48 blocks (i.e. occlude) the airway 28. In some embodiments, the shape of media 48 may be such that upon deployment in the airway 28, a plurality of media 48 interlock and span the airway 28 to collectively occlude the airway 28. The media 48 may have any suitable three dimensional shape including, but not limited to, cubical, triangular, cylindrical, and irregular shapes. In some embodiments, the media 48 may be drug-eluting. That is, the media may include a drug or a chemical that assists in the treatment of the tissue. This drug may promote rejuvenation of the tissue (for example, similar to the drugs discussed above) or may promote necrosis of the tissue (for example, ethanol or another embolic material). It is also contemplated that, in some embodiments, the drug alone may be injected into, or proximate, the tissue at the target site to treat the tissue.

Figure 7B:
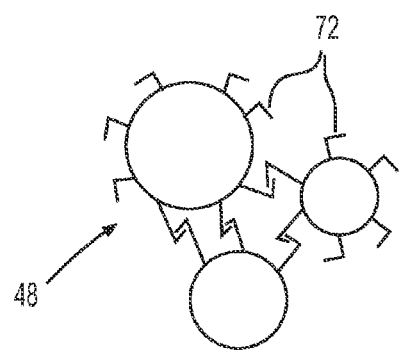
FIG. 7B is a diagrammatic illustration of an exemplary media that may be deployed in an airway of the lung of FIG. 2A.

In some embodiments, the fillers (media 48) may be configured to expand (such as, for example, radially outward) or swell when deployed in the airway 28 (for example, when the fillers come into contact with humidity in the airway 28). In such embodiments, a relatively small-sized filler discharged at a site (for example, a bronchiole 20) may travel downstream and gradually expand to fill an airway 28 (for example, an alveoli 22) downstream of the discharge site. In some embodiments, the media 48 may include expandable microspheres comprising a thermoplastic shell encapsulating a low boiling point liquid hydrocarbon. When the temperature of the microsphere reaches a threshold value, the thermoplastic shell softens. The increasing pressure of the hydrocarbon within the microsphere will then cause the microsphere to expand in volume. In some embodiments, the microsphere dissolves to expose a constrained (unexpanded) state of another material. This material may expand then expand to fill the airway 28. In some embodiments, as illustrated in FIG. 7B, the fillers (expandable or non-expandable media 48) may include surface modifications (such as, for example, velcro loops, barbs 72, or other locking features) that assist in interlocking the fillers together. Alternatively or additionally, these surface modifications may act as anchors to prevent the fillers from separating from tissue after it is implanted. It is contemplated that, in some embodiments, the barbs 72 form on the surface of the filler only after the fillers are deployed in an airway 28. For instance, when the fillers come into contact with humidity in the airway 28, the barbs 72 extend (or disentangle) from the surface of the fillers. In some embodiments, a sticky surface coating on media 48 may serve as an anchor.

Any of the devices discussed with reference to FIGS. 3-6 may be used to deliver the media 48 discussed in the previous paragraphs to a desired treatment site at an airway 28. In an exemplary embodiment, a catheter 40 may be advanced through a natural opening of the body (e.g., via a mouth or nose) into the airway 28 proximate the treatment site. Radiopaque markers 52 on the catheter 40 may assist in positioning the catheter 40 at the desired site. Once suitably positioned, a balloon 32 may optionally be inflated to contact the interior walls of the airway 28 and seal the airway 28 to prevent the media 48 from travelling into adjacent regions of the lung not intended to be treated during the procedure. In some embodiments, the media 48 may be discharged in a stream of pressurized fluid (e.g., air) to achieve better penetration depth into the airway 28. Once a desired amount of the media 48 is discharged at the treatment site (continuously or in batches), the catheter 40 may be moved to a different airway 28 (or a different portion of the same airway 28) for treatment. After all the desired sites are treated, the catheter 40 may be retracted out of the airway.

In some embodiments, an entire portion of an airway may be occluded using media 48. In other embodiments, only a discrete portion of the airway 28 may be occluded. In such embodiments, a space in front of the occluded portion (or beside the occluded portion) may be left open. In some embodiments, instead of occluding an entire area, the media 48 may be used to reduce a cross-sectional area of an airway 28. In some embodiments, air in an airway 28 may be removed prior to being occluded by injecting media 48.

In some embodiments, instead of directly discharging the media 48 into an airway 28, an occluder filled with a suitable media 48 may be positioned in the airway 28 to occlude the airway 28. FIG. 8 illustrates an embodiment in which an occluder, in the form of balloon 62 filled with media 48, is used to occlude the airway 28. In use, a sheath 130 may be introduced into, and suitably positioned at, a desired treatment site in an airway 28. A balloon 62 (in an uninflated or deflated state) may then be delivered to the treatment site through the sheath 130. A catheter 40, introduced to the treatment site through the sheath 130, may then be used to fill the balloon 62 with media 48 and inflate the balloon 62. The inflated balloon 62 may wedge or lock into position on the airway walls and occlude the airway. Any of the previously discussed types of media 48 may be used to fill the balloon 62. In some embodiments, a thermal transition gel may be used as the media 48. In such embodiments, gel in a fluid state may be injected into the balloon 62 to inflate it. Upon cooling, the gel may harden and press the balloon 62 against the airway walls and occlude the airway 28. In some embodiments, sheath 130 may include a detachable tether 132 to detach the balloon 62 from the sheath 130 after filling. It is also contemplated that, in some embodiments, the balloon 62 may include valves or other mechanisms to prevent the media 48 from travelling upstream of the balloon 62 during filling. In some embodiments, the external surface 64 of balloon 62 may be coated with a chemical that helps the surface 64 adhere to tissue and/or assist in necrosis of the tissue.

Although the exemplary embodiments described above have been disclosed in connection with devices for manipulating lung airways, those skilled in the art will understand that the principles set out above can be applied to any bronchial device and can be implemented in different ways without departing from the scope of the disclosure as defined by the claims. In particular, constructional details, including manufacturing techniques and materials, are well within the understanding of those of skill in the art and have not been set out in any detail here. These and other modifications and variations are well within the scope of the present disclosure and can be envisioned and implemented by those of skill in the art.

Moreover, while specific exemplary embodiments may have been illustrated and described herein, it should be appreciated that combinations of the above embodiments are within the scope of the disclosure. Other exemplary embodiments of the present disclosure will be apparent to those skilled in the art from consideration of the specification and practice of the exemplary embodiments disclosed herein. It is intended that the specification and examples be considered as exemplary only, and departures in form and detail may be made without departing from the scope and spirit of the present disclosure as defined by the following claims.

What is claimed is:

1. A method of treating a lung, comprising:
    deploying a catheter into an airway of the lung; and
    discharging a media into the airway through the catheter, wherein the catheter has a bent distal end, and discharging the media includes rotating the bent distal end and moving the bent distal end longitudinally through the airway, the media being configured to expand in the airway and occlude the airway after being discharged from the catheter, wherein the media includes a shell enclosing an expandable material, wherein the bent distal end is coupled to a first threaded member having one or more threads, and wherein rotating the bent distal end includes rotating the first threaded member relative to a second threaded member having one or more threads that are complementary to the one or more threads of the first threaded member.

2. The method of claim 1, wherein the media includes a drug, and the method further includes releasing the drug into the airway from the media after the discharging.

3. The method of claim 1, wherein the shell increases in temperature and softens when discharged into the airway.

4. The method of claim 3, wherein the shell expands via a force expelled by the expandable material after softening.

5. The method of claim 4, wherein the shell is a thermoplastic shell.

6. A method of treating a lung, comprising:
    deploying a catheter into an airway of the lung; and
    depositing a predetermined pattern of a media into the airway through the catheter, the media being a drug suspension in a biodegradable polymer, wherein:
        depositing a predetermined pattern includes depositing a helicoidal pattern, and after the predetermined pattern of the media is deposited into the airway, mucus is able to travel from a portion of the airway distal to an entire portion of deposited media, through a portion of the airway containing the entire portion of deposited media, to a portion of the airway proximal to the entire portion of deposited media;
        depositing the helicoidal pattern includes discharging the media from the catheter while the catheter is rotated, and translated longitudinally through the airway;
        wherein a distal end of the catheter is bent,
        the bent distal end is coupled to a first threaded member having one or more threads; and
        rotating the catheter includes rotating the first threaded member relative to a second threaded member having one or more threads that are complementary to the one or more threads of the first threaded member.

7. The method of claim 6, wherein the biodegradable polymer includes a low glass transition temperature.

8. The method of claim 6, wherein depositing a helicoidal pattern includes discharging the media into the airway in a fluid form, and solidifying the media in the airway.

9. The method of claim 8, wherein discharging the media includes heating the media above a glass transition temperature of the polymer, and solidifying the media includes cooling the media below the glass transition temperature.

10. The method of claim 6, wherein the media is a drug that includes a corticosteroid or a glucosteroid.

11. The method of claim 6, wherein the media is discharged by a delivery device, wherein the delivery device includes a container and a plunger disposed within the container, wherein distal movement of the plunger through the container dispenses the media from the container and through the bent distal end into the airway; and the plunger is coupled to the second threaded member, and distal movement of the plunger causes the first threaded member and the second threaded member to rotate relative to one another.

12. A method of treating a lung, comprising:
    deploying a catheter into an airway of the lung; and
    discharging a media into the airway through the catheter so that the media adheres to a wall of the airway in a helicoidal pattern, wherein the media is discharged with a delivery device having a bent distal end by rotating the bent distal end and moving the bent distal end longitudinally through the airway, wherein the bent distal end is coupled to a first threaded member having one or more threads, and wherein rotating the bent distal end includes rotating the first threaded member relative to a second threaded member having one or more threads that are complementary to the one or more threads of the first threaded member.

13. The method of claim 12, wherein the delivery device includes a container and a plunger disposed within the container, and distal movement of the plunger through the container dispenses the media from the container and through the bent distal end into the airway.

14. The method of claim 13, wherein the plunger is coupled to the second threaded member, and distal movement of the plunger causes the first threaded member and the second threaded member to rotate relative to one another.

15. The method of claim 12, wherein a mucociliary escalator of the airway is not blocked after a point in which all of the media settles in the airway.

* * * * *